United States Patent
Bunel et al.

(10) Patent No.: US 9,193,872 B2
(45) Date of Patent: Nov. 24, 2015

(54) PHOTO-CROSSLINKABLE ANTIFOULING COMPOSITIONS, FILMS OBTAINED FROM SAID COMPOSITIONS, AND CORRESPONDING USES

(75) Inventors: Claude Bunel, Rouen (FR); Irene Campistron, Le Mans (FR); Claire Hellio, Concarneau (FR); Rachid Jellali, Le Mans (FR); Albert Laguerre, Le Mans (FR); Jean-Luc Mouget, Le Mans (FR); Jean-Francois Pilard, Pance (FR)

(73) Assignees: CENTRE NATIONAL DE LA RECHERCHE SCIENTIFIQUE (CNRS), Paris (FR); UNIVERSITE DU MAINE, Le Mans (FR)

( * ) Notice: Subject to any disclaimer, the term of this patent is extended or adjusted under 35 U.S.C. 154(b) by 368 days.

(21) Appl. No.: 13/124,271

(22) PCT Filed: Oct. 8, 2009

(86) PCT No.: PCT/FR2009/051924
§ 371 (c)(1),
(2), (4) Date: Jul. 21, 2011

(87) PCT Pub. No.: WO2010/043800
PCT Pub. Date: Apr. 22, 2010

(65) Prior Publication Data
US 2011/0268689 A1 Nov. 3, 2011

(30) Foreign Application Priority Data

Oct. 14, 2008 (FR) ...................................... 0805680

(51) Int. Cl.
| | | |
|---|---|---|
| C09D 4/00 | (2006.01) |
| A01N 31/02 | (2006.01) |
| A01N 33/12 | (2006.01) |
| A01N 37/06 | (2006.01) |
| A01N 43/20 | (2006.01) |
| C09D 123/22 | (2006.01) |
| C08F 2/50 | (2006.01) |
| C08K 5/00 | (2006.01) |
| C08K 5/06 | (2006.01) |
| C08K 5/07 | (2006.01) |
| C08K 5/11 | (2006.01) |

(52) U.S. Cl.
CPC *C09D 4/00* (2013.01); *A01N 31/02* (2013.01); *A01N 33/12* (2013.01); *A01N 37/06* (2013.01); *A01N 43/20* (2013.01); *C09D 123/22* (2013.01); *C08F 2/50* (2013.01); *C08K 5/0025* (2013.01); *C08K 5/06* (2013.01); *C08K 5/07* (2013.01); *C08K 5/11* (2013.01); *Y10T 428/265* (2015.01)

(58) Field of Classification Search
None
See application file for complete search history.

(56) References Cited

U.S. PATENT DOCUMENTS

| | | | | |
|---|---|---|---|---|
| 4,335,026 A | * | 6/1982 | Balinth | ......................... 524/271 |
| 4,977,220 A | | 12/1990 | Dougherty et al. | |
| 5,171,760 A | | 12/1992 | Kaszas et al. | |
| 5,576,388 A | | 11/1996 | St. Clair et al. | |
| 5,948,863 A | | 9/1999 | St. Clair et al. | |
| 6,649,259 B1 | * | 11/2003 | Hu et al. | ...................... 428/343 |

FOREIGN PATENT DOCUMENTS

EP  1 127 925 A1  8/2001

OTHER PUBLICATIONS

International Search Report, dated Mar. 2, 2010, from corresponding PCT application.

\* cited by examiner

*Primary Examiner* — Bethany Barham
*Assistant Examiner* — Barbara Frazier
(74) *Attorney, Agent, or Firm* — Young & Thompson

(57) ABSTRACT

Photo-crosslinkable antifouling compositions, in particular antibacterial, antifungal and anti-algae ones, which include the combination of at least one telechelic oligoisoprene of a particular formula with an agent for crosslinking the oligoisoprene. The antifouling film is obtained by applying a thin layer of such a liquid composition on a substrate and is crosslinked at room temperature by exposure to visible and/or UV radiations. The film can be used for preventing the occurrence of a biofilm on any surface in a humid or aqueous environment, and can be used as an additive for preparing materials with a view to imparting bacteriostatic and/or bactericidal properties thereto.

19 Claims, No Drawings

PHOTO-CROSSLINKABLE ANTIFOULING COMPOSITIONS, FILMS OBTAINED FROM SAID COMPOSITIONS, AND CORRESPONDING USES

FIELD OF THE INVENTION

This invention relates to cross-linkable antifouling and in particular antibacterial, antifungal and antalgic compositions, the films obtained from these compositions as well as the use of these films in particular for antifouling protection of surfaces immersed in a freshwater environment and in a seawater environment.

BACKGROUND OF THE INVENTION

The phenomenon of fouling corresponds to spontaneous colonization and accumulation of microorganisms, algae and animals on surfaces immersed for a variable period of time in a freshwater environment or in a seawater environment. Fouling is a significant nuisance, in particular for watercraft, because by deteriorating the surface of the hulls, it leads to an increase in maintenance costs and presents resistance to the forward movement of the watercraft, resulting in overconsumption of fuel and a reduction in speed.

To overcome this phenomenon, paints incorporating tributyltin, a very effective biocide, have been used for a number of years. Unfortunately, this molecule and its degradation products, released in the seawater environment, seriously affect ecosystems, which has resulted in their total prohibition since 2008. In addition, these residues, including tin, remain in the sediments of ports and immersion sites of dredged slurry.

By replacing tributyltin, a certain number of products that are in principle less toxic have been used: these are for the most part biocidal molecules of low molecular weight such as halogenated molecules, for example chlorinated derivatives (sold under the names: Seanine 211, Kathon 5287, Dichlofluanid, Daconil, Thiodan, Duron, etc.), metal-based derivatives such as zinc or copper (Zinc pyrithione, Ziram, Dithane, etc.) or nitrogenated heterocyclic derivatives (Irgarol 1051), which are incorporated in the matrix of the coating.

These molecules are, however, slowly released into the aquatic environment, thus producing, by accumulation, a certain toxicity in the environment. The European program REACH encourages abandonment of the addition of any organic product (of the herbicide or pesticide type, such as the derivatives described above) in the antifouling paint formulations. In addition, silicone-based paints have been developed, and admittedly demonstrate efficacy in the antifouling field, but have limited applicability, in particular due to their high production costs.

SUMMARY OF THE INVENTION

An objective of this invention is to propose molecules that are not additives, but actual constituents of the antifouling coating.

More recently, polyurethane-type polymers with a biocidal activity have been developed. However, these polymers are obtained by reacting hydroxy telechelic oligoisoprenes with isocyanates. Aside from the recognized toxicity of the latter, the polymerization reaction requires the addition of stannic catalysts, which are prohibited in antifouling applications. Finally, the implementation is more delicate and therefore presents a major disadvantage in industrial use.

Another objective of this invention is to develop polymer precursors not requiring a complex reaction to produce the polymer coating, with simple and quick implementation, capable of being performed on site.

The inventors have discovered that polymer films with antifouling properties could be prepared from photo-crosslinkable compositions based on certain telechelic oligoisoprenes.

To this end, the invention proposes a cross-linkable antifouling composition, in particular an antibacterial, antifungal and/or antalgic composition,
characterized in that it includes the combination of
at least one telechelic oligoisoprene of general formula (I):

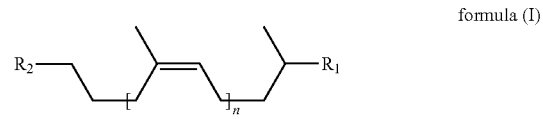

formula (I)

or such an oligoisoprene (I) partially hydrogenated, of formula (II):

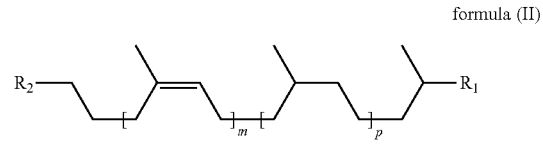

formula (II)

or a partially epoxidized compound of formula (I), of formula (III):

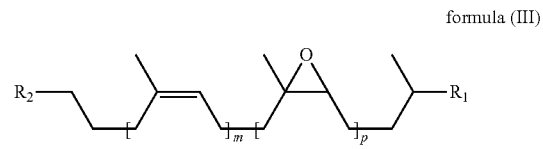

formula (III)

in which formulas:
n is an integer between 5 and 100, preferably between 8 and 70
m and p are integers, less than n, preferably such that $p<m<n$
$R_1$ is a group chosen from: OH, $C_1$ to $C_{12}$ alkoxy, preferably $C_1$ to $C_8$ (for example, methyloxy, ethyloxy or octyloxy), aryloxy (for example, phenyloxy), acryloyl, —$NR_3R_4$ with $R_3$ being H or a $C_1$-$C_{12}$ linear alkyl and $R_4$ being H or a $C_1$-$C_{12}$ linear alkyl
$R_2$ is a group chosen from: OH, acryloyl, —$NR_5R_6$ or —$N^+R_5R_6R_7$ with $R_5$ and $R_6$, identical or different, being chosen from: H, alkyl hydroxyalkyl, cyanoalkyl and halogenoalkyl in $C_1$-$C_{12}$, in which $R_7$ is a $C_6$-$C_{15}$ linear alkyl,
and at least one cross-linking agent of said telechelic oligoisoprene.

DETAILED DESCRIPTION OF THE INVENTION

The oligoisoprene according to the invention is advantageously in the form of a liquid at room temperature, namely preferably between 5 and 35° C. (or a range of possible usage temperatures).

This oligoisoprene can be prepared from natural or synthetic rubber, having the advantage of possessing microstructures that can be chemically modified in a controlled manner. Its basic backbone is linear cis-1,4-polyisoprene obtained from non-toxic compounds (natural rubber). This cis-1,4-polyisoprene advantageously has a functionality equal to 2.

It is thus capable of being spread on a support in a thin layer, and, in the presence of a cross-linking agent, of polymerizing by visible and/or ultraviolet radiation, forming a flexible film.

It has been discovered that such a composition has biostatic properties, i.e. inhibiting the proliferation of living organisms on said surface, or biocidal properties, namely enabling any biological organisms in contact with the surface of the support to be destroyed.

The cross-linking agent is present in "catalytic" proportions, i.e. in proportions preferably up to 5% by weight of said compositions.

According to a first embodiment of the invention, in order to adjust the viscosity of the composition according to the invention and enable good spreading on the support, the latter may also include a photo-cross-linkable reactive diluting agent, advantageously under the same conditions as the oligoisoprene. Examples of diluting agents are TMPO (2-ethyl-2-(hydroxymethyl) oxetane) and HDDA (hexane diol diacrylate). This reactive diluting agent enables a substantial increase in reactivity, i.e. the polymerization rate which reduces the time and energy necessary to produce a coating. In addition, this agent significantly reduces the viscosity of the formulation, thereby facilitating its application on the surface to be treated. It is present in proportions of up to 40% by weight of the composition according to the invention.

According to a second embodiment of the invention, the composition does not contain a reactive diluting agent and consists solely of the combination of at least said linear telechelic oligoisoprene of formula (I), (II) or (III) and at least one cross-linking agent of said telechelic oligoisoprene.

However, the composition can also contain "neutral" constituents, i.e. not involved in the photo-cross-linking, such as dyes, pigments, active principles, metal particles, magnetic particles and reinforcing agents.

This invention also relates to an antifouling film, characterized in that it is obtained by applying a thin film of the liquid composition as described above onto a support and cross-linked by visible and/or ultraviolet radiation. This radiation can be provided by a continuous or discontinuous emission lamp, emitting at wavelengths between around 200 nm and 800 nm.

The films thus obtained are transparent or translucent, capable of being colored by the addition of pigments. In addition, they can be flexible (elastic) or rigid according to the quantity and nature of the diluent used. The surface roughness of the films can be controlled by controlling the cross-linking speed, in particular by means of the type of lamp used, by adjusting the dilution rate and the viscosity. Indeed, the higher the cross-linking speed, the greater the roughness of the film formed.

The film obtained surprisingly has biocidal or biostatic properties in particular with respect bacteria, fungi, microalgae and/or macroalgae, regardless of the degree of roughness of the surface. Such a film can thus coat surfaces intended to be immersed, such as watercraft hulls.

This invention also relates to any support coated with a film according to the present invention, in which the total thickness of said film is less than one millimeter, and is preferably between 10 μm and 500 μm.

Thus, the film according to the invention can advantageously be used for antifouling protection of a support immersed in freshwater or seawater, in particular watercraft hulls, in order to inhibit the appearance of a biofilm on medical instruments, catheters or implants, on walls in contact with an aqueous medium or in a moist environment, such as floor covering surfaces, external walls, pipelines, immersed apparatuses (in particular immersed optical apparatuses) or cooling tours. This list is not exhaustive.

This invention also relates to the use of the antifouling composition described above, as an additive in the preparation of materials, in order to confer bacteriostatic and/or bactericidal properties thereon; or in the medical field, in particular in order to produce medical instruments, biomaterials, catheters, prostheses and implants; or to produce coverings, packaging containers, in particular in the agrifood field.

This invention will be described in greater detail and illustrated with the following non-limiting examples.

EXAMPLES

I. Photo-Cross-Linkable Oligoisoprene Syntheses

The synthesis of photo-cross-linkable precursors is performed in a plurality of steps. First, the controlled degradation of 100% linear cis-1,4-polyisoprene, with a functionality equal to 2, provides access to a carbonyl telechelic oligoisoprenes with a well defined number average molar mass and chemical structure. Then, a plurality of chemical modifications on these oligomers produce the various photo-cross-linkable precursors.

All of the synthesized products are characterized by $^1$H-NMR, $^{13}$C-NMR, IRTF, and Steric Exclusion Chromatography.

Mode 1

I.1 Chemical Modifications of Carbonyl Telechelic cis-1,4-polyisoprene (CTPI)

I.1.1 Examples 1 to 4

Reduction of Aldehyde and Ketone Ends: Synthesis of cis-1,4-hydroxy Telechelic Polyisoprene (HTPI)

In a three-neck round-bottom flask equipped with a coolant and magnetic stirring, the CIPI dissolved in THF (0.07 mol/L) is added drop-by-drop to a sodium borohydride solution (NaBH$_4$) in THF (0.3 mol/L). The reaction mixture is then heated to 60° C. After 6 h, it is cooled and hydrolyzed with 20 g of ice dissolved in 20 ml, of THF, poured drop-by-drop by means of an adding ampoule. After a washing with a saturated sodium chloride (NaCl) solution, the organic phase is dried with MgSO$_4$, filtered and concentrated with the rotary evaporator. The product obtained is then dried in a vacuum.

The process conditions and yields obtained are presented in table 1.

TABLE 1

| Examples | CTPI | NaBH$_4$ (g) | T (° C.) | T (h) | Yield (%) |
|---|---|---|---|---|---|
| 1 | 10 | 2.18 | 60 | 6 | 98 |
| 2 | 8 | 1.72 | 60 | 6 | 93 |
| 3 | 13 | 2.84 | 60 | 6 | 94 |
| 4 | 7 | 1.53 | 60 | 6 | 97 |

The $^1$H-NMR of the product obtained (HTPI) gives:

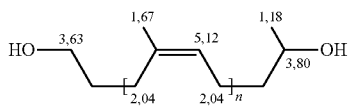

with a number average molar mass between 700 and 5000, in which n is between 9 and 65.

I.1.2 Example 5

Hydrogenation of the HTPI: Synthesis of cis-1,4-hydrogenated Polyisoprene (HHTPI)

In a catalytic hydrogenation device, 2 g of HTPI are introduced, obtained according to one of examples 1 to 4, dissolved in 50 mL of ethyl acetate and 500 mg of palladium supported on carbon (Pd/C). The reaction mixture is subjected to mechanical stirring under hydrogen pressure (3 bars). The time and temperature of the reaction were varied so as to obtain different hydrogenation rates (up to around 83%). The palladium is then separated by filtration, the solution is concentrated with the rotary evaporator and the final product is dried in a vacuum. The yield obtained is 75%.

The product obtained is characterized by $^1$H-NMR:

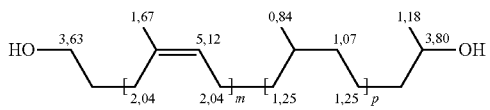

Mode 2

I.1.3 Examples 6 to 9

Synthesis of cis-1,4-amino Carbonyl Telechelic Polyisoprene from CTPI

The reductive amination of the CTPI is performed selectively on the aldehyde function only.

In a three-neck round-bottom flask equipped with magnetic stirring and a coolant in an inert atmosphere, the CTPI in solution is introduced into dichloromethane (0.03 mol/L) and amine (2.1 equivalents). Then, sodium triacetoxyborohydride (NaBH(OAc)$_3$) (2.1 equivalents) is added to the solution. After 24 h at room temperature, the mixture is washed with a soda solution (NaOH, 1N). The organic phase is then separated, dried with MgSO$_4$ and the solvent is evaporated.

The process conditions and yields obtained are presented in table 2.

TABLE 2

| Examples | CTPI (g) | $M_{CTPI}$ (g/mol) | Amine (mL) | NaBH(OAc)$_3$ (g) | Yield (%) |
|---|---|---|---|---|---|
| 6 | 8 | 1700 | Diethyliminodi-acetate: 1.73 | 2.72 | 98 |
| 7 | 5.42 | 1700 | Diethylamine: 0.96 | 1.96 | 80 |
| 8 | 6 | 4500 | Diethylamine: 0.41 | 0.83 | 90 |
| 9 | 12 | 4500 | Diethanolamine: 0.53 | 1.56 | 85 |

The products obtained are, for example:

I.1.4 Examples 10 to 13

Reduction of Carbonyl Functions of Aminocarbonyl Telechelic Oligoisoprenes

In a three-neck round-bottom flask in an inert atmosphere, an etherate-aluminum lithium hydride solution (LiAlH$_4$) at 1 mmol/mL (2 equivalents per polymer mole) is diluted in 10 mL of dry ether. Then, the aminocarbonyl telechelic oligoisoprene dissolved in anhydrous ether (0.01 mol/L) is added drop-by-drop. After 6 h under stirring and at room temperature, the excess aluminum lithium hydride is removed by hydrolysis and the product is extracted with dichloromethane. Finally, the organic phase is separated, dried with MgSO4 and the solvent is evaporated by means of a rotary evaporator.

The details of the process and the yields obtained are presented in table 3.

TABLE 3

| Examples | Oligomer (g) | $M_{oligomer}$ (g/mol) | LiAlH$_4$ (mL) | Yield (%) |
| --- | --- | --- | --- | --- |
| 10 | Oligomer 3 (4.29) | 1700 | 6.2 | 90 |
| 11 | Oligomer 1 (7.91) | 1700 | 9.1 | 70 |
| 12 | Oligomer 3 (4.41) | 4500 | 2.38 | 88 |
| 13 | Oligomer 2 (5.12) | 4500 | 2.76 | 74 |

In particular, the following is obtained:

(4)

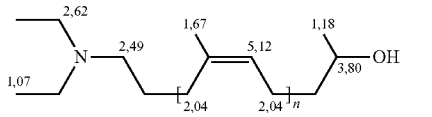

(5)

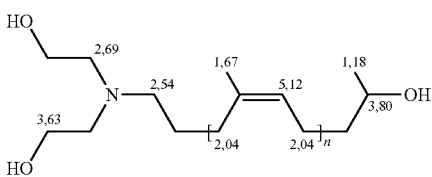

I.1.5 Examples 14 and 15

Synthesis of α-Propyl Amino, ω-Amino Dihydroxyethyl cis-1,4-polyisoprene from Oligoisoprene (2)

In a three-neck round-bottom flask in an inert atmosphere, and equipped with magnetic stirring, oligoisoprene (2) dissolved in dichloromethane (0.022 mol/L) and diethyl aminopropylamine (2.1 equivalents) is introduced. Then, sodium triacetoxyborohydride (2.1 equivalent(s)) and glacial acetic acid (1 equivalent) are added. The reaction is maintained for 24 h at room temperature. Finally, the reaction mixture is washed with a soda solution (1 N) and the organic phase is separated, dried on magnesium sulfate, filtered and concentrated with the rotary evaporator.

The details of the process are presented in table 4:

TABLE 4

| Examples | Oligomer 2 (g) | Diethylamino-propylamine (mL) | NaBH(OAc)$_3$ (g) | Acetic acid (mL) | Yield (%) |
| --- | --- | --- | --- | --- | --- |
| 14 | 18 | 1.93 | 3.6 | 0.3 | 80 |
| 15 | 7.28 | 0.77 | 1.44 | 0.12 | 78 |

The $^1$H-NMR gives:

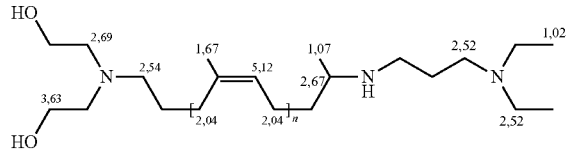

II.2.6 Examples 16 to 18

Partial Epoxidation of Telechelic Oligoisoprenes

Regardless of the telechelic oligomer to be epoxidized, the process is the same. The amount of mCPBA needed is calculated by using the following equation:

$$m_{mCPBA}=(m_{oligomer})/68.8*(T_e/100)*n*M_{mCPBA}*(100/70)$$

with $T_e$: Epoxidation rate (70/100): Purity of in mCPBA (68.8): Molar mass of an isoprene unit n: Number of isoprene patterns The reaction is performed in a three-neck round-bottom flask equipped with magnetic stirring and placed in an ice bath. The oligomer dissolved in the dichloromethane (0.09 mol/L) is introduced into the flask and left under stirring for 30 min to reach a temperature of 0° C. The desired amount of epoxidation agent, in this case mCPBA (meta-chloroperbenzoic acid) (according to the desired epoxidation rate) in solution in 20 mL of CH$_2$Cl$_2$ is then added drop-by-drop to the oligomer solution (see details in table 5). After the addition, the reaction mixture is stirred for 3 h at room temperature, then washed with a saturated sodium hydrogen carbonate solution. Finally, the organic phase is dried on MgSO$_4$, filtered and concentrated. The concentrated product is dried in a vacuum for 24 h.

Concerning the aminotelechelic oligoisoprenes, washing with 5 N soda is performed after the reaction in order to regenerate the amine. Indeed, during the reaction, the tertiary amine is protonated.

TABLE 5

| Examples | Oligomer 2 (g) | $M_{oligomer}$ (g/ml) | mCPBA (g) | $T_e$ (%) | Yield (%) |
| --- | --- | --- | --- | --- | --- |
| 16 | HTPI (4.35) | 1700 | 1.46 | 10 | 95 |
| 17 | HTPI (5) | 4500 | 1.73 | 10 | 92 |
| 18 | Oligomer 4 (5) | 1700 | 1.73 | 10 | 89 |

The ¹H-NMR gives:

| Starting product | Product obtained |
|---|---|
| HTPI | EHTPI: HO—[CH₂(3.63)—C(CH₃)(1.67)=CH(5.12)—CH₂(2.04)]ₘ—[CH₂—C(CH₃)(1.29)—CH(2.69)(O epoxide)—CH₂(1.43)]ₚ—CH(3.80)(CH₃ 1.18)—OH |
| HHTPI | EHHTPI: HO—[CH₂(3.63)—C(CH₃)(1.67)=CH(5.12)—CH₂(2.04)]ₘ—[C(CH₃)(1.29)—CH(2.69)(O)—CH₂(1.43)]ₚ—[CH(CH₃ 0.84)(1.07)—CH₂(1.25)]_q—CH(3.80)(CH₃ 1.18)—OH |
| oligomer 4 | (6): (CH₃CH₂ 3.14)—N(CH₂ 2.54)—[CH₂—C(CH₃)(1.67)=CH(5.12)—CH₂(2.04)]ₘ—[C(CH₃)(1.29)—CH(2.69)(O)—CH₂(1.43)]ₚ—CH(2.67)(CH₃ 1.07)—OH; (3.29) |
| oligomer 5 | (7): HO—CH₂CH₂(3.14)—N(CH₂ 2.54)—[CH₂—C(CH₃)(1.67)=CH(5.12)—CH₂(2.04)]ₘ—[C(CH₃)(1.29)—CH(2.69)(O)—CH₂(1.43)]ₚ—CH(2.67)(CH₃ 1.07)—OH; HO—CH₂CH₂(3.29) |

II.2.7 Examples 19 to 22

Attachment of Acrylate Functions at the Chain Ends

In a three-necked round-bottom flask placed in a bath at 0° C.; and under argon circulation, the oligomer is introduced in solution in anhydrous dichloromethane (0.08 mol/L). Then, triethylamine (2.3 equivalents, except for oligomer 5 (3.5 equivalents)) is added, then acryloyl chloride (2.3 equivalents, except for oligomer 5 (3.5 equivalents)) is added drop-by-drop (see details in table 6). The mixture is left under stirring and at room temperature for 24 h. At the end of the reaction, it is washed with a soda 1 N solution, then the organic phase is dried on magnesium sulfate, filtered and concentrated. The product is dried in a vacuum for 24 h.

TABLE 6

| Examples | Oligomer (g) | Acryloyl chloride (mL) | Triethylamine (mL) | Yield (%) |
|---|---|---|---|---|
| 19 | HTPI (7.25) | 0.88 | 1.5 | 92 |
| 20 | Oligomer 4 (3.86) | 0.45 | 0.77 | 88 |
| 21 | Oligomer 5 (5.52) | 0.96 | 1.65 | 85 |
| 22 | Oligomer 6 (3.20) | 0.34 | 0.59 | 85 |

| Starting product | Product obtained |
|---|---|
| HTPI | (8): CH₂=CH—C(=O)—O—CH₂(4.2)—[C(CH₃)(1.67)=CH(5.12)—CH₂(2.04)]ₙ—CH(5.01)(CH₃ 1.2)—O—C(=O)—CH=CH₂ (6.15, 5.8, 6.42) |

-continued

| Starting product | Product obtained |
|---|---|
| HHTPI | 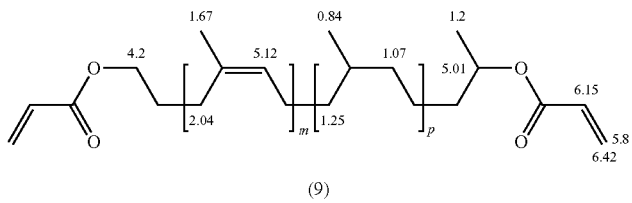<br>(9) |
| EHTPI | 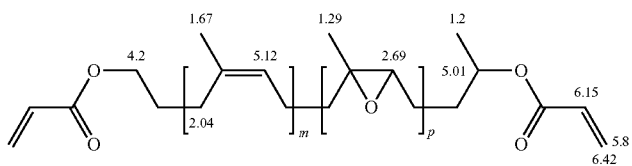<br>(10) |
| oligomer 4 | 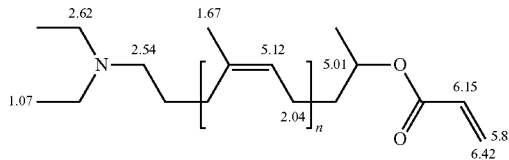<br>(11) |
| oligomer 5 | 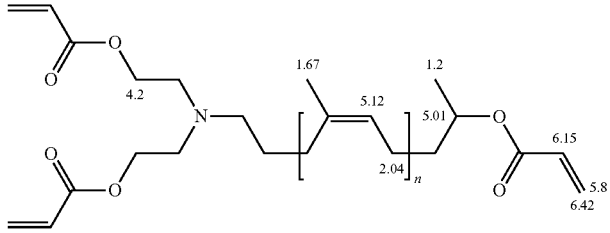<br>(12) |
| oligomer 6 | 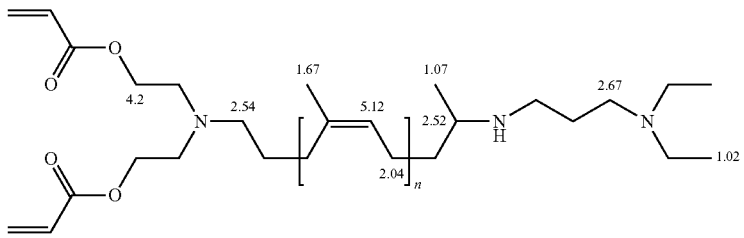<br>(13) |

$^1$H-NMR:

I.1.8 Examples 23 to 25

Quaternization of Amine Functions of Aminotelechelic Oligoisoprenes

In a three-necked round-bottom flask placed in a heating bath, the oligomer to be treated (see table 7), dissolved in a dichloromethane/acetonitrile (3/1) (0.02 mol/L), is introduced. Then, the alkyl halogenide is added (5 equivalents/ amine function) and the reaction mixture is heated to 40° C. in the case of octyl iodide and to 65° C. in the case of octyl bromide. After 24 h, the solvents are evaporated with the rotary evaporator and the excess alkyl halogenide is removed by high vacuum evaporation.

TABLE 7

| Examples | Oligomer (g) | Triethylamine (mL) | Yield (%) |
|---|---|---|---|
| 23 | oligomer 6 (4.2) | 0.8 | 100 |
| 24 | oligomer 11 (2.3) | 0.55 | 100 |
| 25 | oligomer 13 (10) | 6.2 | 100 |

The $^1$H-NMR gives:

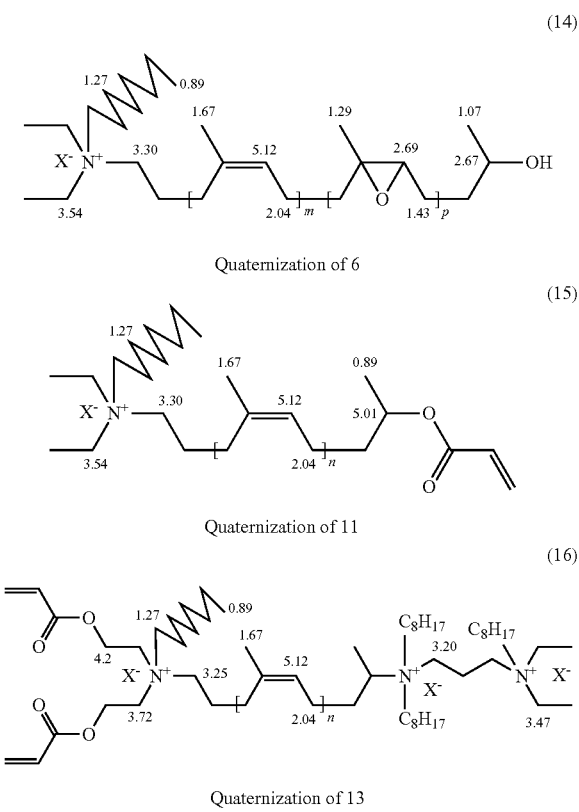

Quaternization of 6

Quaternization of 11

Quaternization of 13

II. Example 26

Preparation of Coatings by Photo-Cross-Linking

The different coatings are prepared either by using only one of the precursors described above or in the presence of reactive diluents. Examples of some formulations are described in table 8 below.

TABLE 8

| Formulation No. | Precursor | Photo-initiator (%)* | Diluent (%)** | Photo-cross-linking mode |
|---|---|---|---|---|
| 1 | EHTPI | Degacure KI85 5% | — | Cationic |
| 2 | EHTPI | Degacure KI85 5% | TMPO 30% | Cationic |
| 3 | EHTPI + oligomer 14 (50/50) | Degacure KI85 5% | — | Cationic |
| 4 | oligomer 8 | Darocur 1173 3% | — | Free radical |
| 5 | oligomers (8 + 15) (50/50) | Darocur 1173 3% | — | Free radical |
| 6 | oligomers (8 + 15) (75/25) | Darocur 1173 3% | — | Free radical |
| 7 | oligomers (8 + 14) (50/50) | Darocur 1173 3% | — | Free radical |
| 8 | oligomer 9 | Darocur 1173 3% | HDDA 30% | Free radical |

*Mass percent with respect to the mass of the precursor or precursor + diluent
**Mass percent with respect to the total mass of the mixture The photo-initiators and diluents used in this example are presented below:

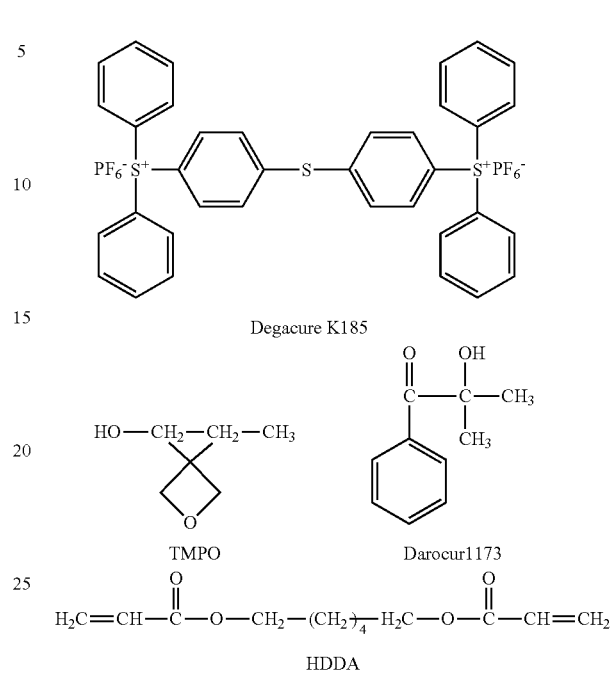

Degacure K185

TMPO          Darocur1173

HDDA

The formulations are spread on a support by means of Conway bars, which makes it possible to control the thickness of the coatings capable of ranging from 10 µm to 500 µm. The irradiation intensities are 50 and 13 mW/cm$^2$, respectively, for the cationic and free radical polymerization.

In the conditions described above, the coatings obtained by the free radical mode have roughnesses between 15 and 20 Å and those obtained by cationic mode have a greater roughness (between 40 and 45 Å).

The supports, which are glass, metal or Plexiglas, were tested.

The adhesion on these different surfaces was excellent, by contrast with the comparative trials performed on polyurethane-based films, which swelled in an aqueous medium and separated from the supports.

Tests Evaluating Antifouling Properties

Formulations 1 to 8 above were tested with respect to marine organisms which are indicators of biofouling and commonly used for laboratory tests: bacteria, fungi, microalgae and macroalgae. Each biological test was performed at least six times in order to ensure the reputability of the results.

Placing the Coatings in Contact with the Bacteria

The marine bacteria selected for this work (*Pseudoalteromonas elyakovii Shewanella putrefaciens, Cobetia marina, Polaribacter irgensil and Vibrio aestuarianus*) are recognized as major components of marine biofilms. The evaluation of the potential antimicrobial activity of the formulations was performed by the classic microplate method. The bacteria were cultivated on the MHB medium (Mueller Hinton Broth, SIGMA) enriched with NaCl (15 g/l). The films, cut by means of a punch, were deposited in the wells of a microplate (Fisher, 96 wells). The seeding of the microplates was then performed: 100 µL of a bacterial suspension containing 2.10$^8$ cells/mL were deposited in each well in a sterile manner. After incubation (48 h at 30° C.), the antimicrobial activity was observed by comparison of the bacterial growth between the formulations and the control (C).

In the first screening series, three bacterial strains were chosen (*Pseudoalteromonas elyakovii, Shewanella putrefaciens, Cobetia marina*). The results presented in table 9 (first series of tests) show, by comparison with the control, that formulations 1-3 and 5-7 enable inhibition of the growth of the three strains tested. Formulations 4 and 8 have antibacterial properties with respect to two of the three strains selected. This clearly demonstrates the antibacterial character of the films of this invention.

TABLE 9

|  | 1 | 2 | 3 | 4 | 5 | 6 | 7 | 8 | C |
|---|---|---|---|---|---|---|---|---|---|
| *Pseudoalteromonas elyakovii* | + | + | + | − | + | + | + | + | − |
| *Shewanella putrefacients* | + | + | + | + | + | + | + | − | − |
| *Cobetia marina* | + | + | + | + | + | + | + | + | − |

A second series of tests was performed, in which the bacteria presented in table 10 were placed in the presence of films of formulation 1, 4 and 7 and the control.

A portion of films 4 and 7 was first subjected to an "extraction", i.e. washing with dichloromethane at reflux at 40° C. for 24 hours in order to remove any precursors remaining on said films. The results obtained are presented in table 10.

TABLE 10

|  | 1 | 4 | 4 (extraction) | 7 | 7 (extraction) | C |
|---|---|---|---|---|---|---|
| *Pseudoalteromonas elyakovii* | + | + | + | + | + | − |
| *Shewanella putrefacients* | + | + | + | + | + | − |
| *Cobetia marina* | + | + | + | + | + | − |
| *Polaribacter irgensii* | + | + | + | + | + | − |
| *Vibrio aestuarianus* | + | + | + | + | + | − |

Key to Tables 9 and 10
Fi: no. film
C: control (reference surface: polystyrene)
(+): presence of an inhibition halo, zone in which the bacteria do not cross over or under the film
(−): the bacteria, push over and/or under the films
No difference in efficacy was observed between films 4 and 7 subjected to extraction or not. The "antibacterial" action is not therefore due to any presence of residues.

Placing the Films in Contact with the Microalgae

The phytoplanctonic algae selected (*Amphora caffeaeformis, Cylindrotheca closterium, Pleurochrysis roscoffensis, Chlorarachnion globosum, Navicula jeffreyi* and *Exanthemachrysis Gayraliae*) were chosen for their importance in biofouling phenomena in a seawater environment and for their capacity to form EPS (exopolysaccharides playing a crucial role in the permanent attachment of biofilms). The inhibition of their attachment and growth is therefore a major challenge for the development of new antifouling solutions.

The evaluation of the antimicroalgae potential of the different films 1 to 8 was performed by the microplate method. The strains are cultivated on the F/2 medium. The films cut by means of a punch were deposited in the wells of a microplate (Fisher, 96 wells). The seeding of the microplates was then performed: 100 µl of an algae suspension containing 1 µg/mL of chlorophyll were deposited in each well in a sterile manner. After incubation (5 days at 25° C.), the anti-microalgae activity was observed by optical microscopy, and the count of the adhering microalgae was performed on thirty different optical fields. The average of the algae attached per surface unit is then determined.

Table 11 below shows the percentage (%) of adhering cells on the films with respect to the number of adhering cells on the reference surface (C).

TABLE 11

|  | 1 | 2 | 3 | 4 | 5 | 6 | 7 | 8 | C |
|---|---|---|---|---|---|---|---|---|---|
| *Amphora coffeaeformis* | 4 | 6.3 | 2.36 | 2.1 | 1.1 | 1.2 | 1 | 4.2 | 100 |
| *Cylindrotheca closterium* | 3 | 4.6 | 2.75 | 2.3 | 1.07 | 0.76 | 0.95 | 3.76 | 100 |
| *Pleurochrysis Roscoffensis* | 4.2 | 4.5 | 1.44 | 1.85 | 1 | 0.87 | 0.7 | 4 | 100 |
| *Chlorarachnion glosobosum* | 3.1 | 3.5 | 1.7 | 1 | 1.05 | 1.2 | 2.9 | 2.6 | 100 |
| *Navicula jeffreyi* | 1.8 | 3 | 1.7 | 1.83 | 1.3 | 1.22 | 0.9 | 2 | 100 |
| *Exanthemachrysis Gayraliae* | 1.3 | 2 | 1.1 | 1.4 | 0.75 | 1.2 | 1 | 1.6 | 100 |

Placing the Coatings in Contact with the Macroalgae

The algae used *Ulva intestinalis*, an opportunistic green algae and one of the species most heavily involved in marine fouling. It was collected the day of the tests on the coast of Portsmouth (Great Britain).

The fertile parts (in sporulation) of the algae are selected and placed in a Von Stosch medium. After several minutes, the spores are released in the medium, and their presence is controlled by observation with an optical microscope.

The polymer film samples are cut into small circles as above and placed in a 96-well microplate. Then, 100 µL of the medium containing 25,000 spores are injected into each well (concentration of 250,000 spores/mL). Empty wells are used as references (C) and six replicates are produced for each sample. The plates are placed in the dark for two hours in order to enable the spores to attach.

After two hours, the wells are emptied and rinsed with the Von Stosch solution in order to remove the unattached spores, then 100 µL of the medium are added. The plates are placed in an incubator at 15° C., under illumination of 45 µmoles photons $m^{-2}s^{-1}$ (photo-period: 16 hours of light/8 hours of darkness) for one week.

The observations are performed by optical microscopy. The count of attached spores as well as that of the germinated spores were performed on thirty different optical fields. Averages of attached/or germinated spores per surface unit are then determined and presented in table 12.

*Ulva intestinalis*

TABLE 12

| Film | 1 | 4 | 4 (extraction) | 7 | 7 (extraction) | C |
|---|---|---|---|---|---|---|
| Adhering spores/cm$^2$ | 3120 | 35 | 59 | 21 | 32 | 11800 |
| Percentage/control | 27% | 0.3% | 0.5% | 0.17% | 0.27% | 100% |
| Germinated spores | 1090 | 0 | 0 | 0 | 0 | 9500 |
| % spores germinated with respect to fixed spores | 35% | 0% | 0% | 0% | 0% | 85% |

By inhibiting almost all of the spore adhesion and the germination thereof, films 4 and 7 appear to be excellent anti-algae, with regard to *Ulva intestinalis*.

The adhesion and the growth of this algae is also strongly inhibited on film no. 1.

Placing the Coatings in Contact with Fungi

The antifungal activity of the films was tested, using the method described by Hellio et al. (2000, Appl. Microbiology and Biotechnology, 54, 543-549), with regard to five marine fungal strains of the culture collection of the University of Portsmouth (School of Biological Sciences—Great Britain).

*Halosphaeriopsis mediosetigera*

*Asteromyces cruciatus*

*Lulworthia uniseptata*

*Zalerion sp*

*Monodietys pelagica*

The fungal strains were cultivated on inclined corn agar. Each flexible film sample was incorporated in 200 µL of corn agar at 12%, pH 6 (Sigma). The test plate was inoculated in a sterile medium at, the center with a pellet 2 mm in diameter of agar containing mycelium. All of the tests were performed in duplicate. After incubation at 25° C. for four weeks, the activity was evaluated by observing the growth of the fungal colonies. The results are presented in table 13.

TABLE 13

|  | 1 | 4 | 4 (extraction) | 7 | 7 (extraction) | C |
|---|---|---|---|---|---|---|
| *Halosphaeriopsis mediosetigera* | − | + | + | + | + | − |
| *Asteromyces cruciatus* | − | + | + | + | + | − |
| *Lutworthia uniseptata* | − | + | + | + | + | − |
| *Zalerion sp* | − | + | + | + | + | − |
| *Monodictys pelagica* | − | + | + | + | + | − |

−=normal growth=no differences with the control

+=inhibition of growth

Films 4 and 7 are also excellent antifungal agents.

The invention claimed is:

1. A photo-cross-linkable composition, comprising:
at least one compound selected from the group consisting of:
a telechelic cis-1,4-oligoisoprene of general formula (I):

$$R_2 \cdots \cdots R_1, \quad (I)$$

a partially hydrogenated cis-1,4-oligoisoprene of formula (II):

$$R_2 \cdots \cdots R_1, \quad (II)$$

and a partially epoxidized cis-1,4-compound of formula (III):

$$R_2 \cdots \cdots R_1, \quad (III)$$

wherein:
n is an integer between 5 and 100,
m and p are integers, and are less than n,
$R_1$ is a group selected from: OH, $C_1$ to $C_{12}$ alkoxy, aryloxy, acryloyl, and —$NR_3R_4$, with $R_3$ and $R_4$ independently being H or a $C_1$-$C_{12}$ linear alkyl
$R_2$ is a group selected from: OH, acryloyl, —$NR_5R_6$, and —$N^+R_5R_6R_7$, with $R_5$ and $R_6$ independently being selected from: H, alkyl, hydroxyalkyl, cyanoalkyl and halogenoalkyl in $C_1$-$C_{12}$, and $R_7$ is a $C_6$-$C_{15}$ linear alkyl; and
at least one cross-linking agent, wherein the cross-linking agent is Degacure KI85

Darocur1173 or, or a combination thereof,
wherein a film formed from said composition has antifouling properties.

2. The composition according to claim 1, wherein the oligoisoprene is in liquid form at a temperature of between 5° C. to 35° C.

3. The composition according to claim 1, further comprising a photo-cross-linkable reactive diluent.

4. The composition according to claim 1, consisting of the at least one compound and the at least one cross-linking agent.

5. The composition according to claim 1, further comprising one or more additive selected from the group consisting of dyes, pigments, active principles, metal particles, magnetic particles, and reinforcing agents.

6. An antifouling film, obtained by applying a thin film of the composition according to claim 1 onto a support and cross-linked by visible and/or ultraviolet radiation.

7. The film according to claim 6, wherein the film has biocidal or biostatic properties with respect to bacteria, fungi, microalgae and/or macroalgae.

8. A support coated with the film according to claim 6, wherein the film has a thickness of between 10 μm to 500 μm.

9. A method of inhibiting the appearance of a biofilm on medical instruments, catheters or implants, on walls in contact with an aqueous medium or in a moist environment, comprising applying the antifouling film according to claim 6 to said medical instruments, catheters, implants, walls, floor covering surfaces, external walls, pipelines, or cooling tours.

10. A method of conferring bacteriostatic and/or bactericidal properties to materials, comprising adding the composition of claim 1 to said materials and photo-crosslinking the composition to form a film on said material.

11. The method according to claim 10, wherein said materials are selected from the group consisting of medical instruments, biomaterials, catheters, prostheses and implants.

12. The method according to claim 10, wherein said materials are coverings or packaging containers in the agrifood field.

13. A method for the antifouling protection of a support immersed in freshwater or seawater, comprising applying to said support the antifouling film according to claim 6.

14. The method of claim 13, wherein the support is a watercraft hull.

15. The composition according to claim 1, wherein n is an integer between 8 and 70.

16. The composition according to claim 1, wherein p≤m≤n.

17. The composition according to claim 1, consisting essentially of the at least one compound and the at least one cross-linking agent of said compound.

18. The composition according to claim 3, wherein the photo-cross-linkable reactive diluent is HO—$CH_2$—$CH_2$—$CH_3$ or

TMPO $H_2C$=CH—$\overset{O}{\overset{\|}{C}}$—O—$CH_2$—$(CH_2)_4$$H_2C$—O—$\overset{O}{\overset{\|}{C}}$—CH=$CH_2$,

HDDA or, or a combination thereof.

19. A photo-cross-linkable composition, comprising:
at least one compound selected from the group consisting of:
a telechelic cis-1,4-oligoisoprene of general formula (I):

(I)

$R_2$—[...]$_n$—$R_1$, a partially hydrogenated cis-1,4-oligoisoprene of formula (II):

(II)

$R_2$—[...]$_m$—[...]$_p$—$R_1$, and
a partially epoxidized cis-1,4-compound of formula (III):

(III)

$R_2$—[...]$_m$—[...]$_p$—$R_1$, wherein:
n is an integer between 5 and 100,
m and p are integers, and are less than n,
$R_1$ is a group selected from: OH, $C_1$ to $C_{12}$ alkoxy, aryloxy, acryloyl, and —$NR_3R_4$, with $R_3$ and $R_4$ independently being H or a $C_1$-$C_{12}$ linear alkyl,
$R_2$ is a group selected from: OH, acryloyl, —$NR_5R_6$, and —$N^+R_5R_6R_7$, with $R_5$ and $R_6$ independently being selected from: H, alkyl, hydroxyalkyl, cyanoalkyl and halogenoalkyl in $C_1$-$C_{12}$, and $R_7$ is a $C_6$-$C_{15}$ linear alkyl;
at least one cross-linking agent of said at least one compound, wherein said cross-linking agent is not an isocyanate; and
a photo-cross-linkable reactive diluent, wherein the photo-cross-linkable reactive diluent is HO—$CH_2$—$CH_2$—$CH_3$ or

TMPO $H_2C$=CH—$\overset{O}{\overset{\|}{C}}$—O—$CH_2$—$(CH_2)_4$$H_2C$—O—$\overset{O}{\overset{\|}{C}}$—CH=$CH_2$,

HDDA or, or a combination thereof, and
wherein a film formed from said composition has antifouling properties.

* * * * *